US011096713B2

United States Patent
Ahn

(10) Patent No.: US 11,096,713 B2
(45) Date of Patent: Aug. 24, 2021

(54) SURGICAL DEVICE FOR SKIN THERAPY AND NEEDLE MODULE FOR SKIN THERAPY

(71) Applicant: AGNES MEDICAL CO., LTD., Seongnam-si (KR)

(72) Inventor: Gunyoung Ahn, Seongnam-si (KR)

(73) Assignee: AGNES MEDICAL CO., LTD., Seongnam-si (KR)

(*) Notice: Subject to any disclaimer, the term of this patent is extended or adjusted under 35 U.S.C. 154(b) by 300 days.

(21) Appl. No.: 16/473,580

(22) PCT Filed: Dec. 30, 2016

(86) PCT No.: PCT/KR2016/015579
§ 371 (c)(1),
(2) Date: Jun. 25, 2019

(87) PCT Pub. No.: WO2018/124348
PCT Pub. Date: Jul. 5, 2018

(65) Prior Publication Data
US 2019/0328418 A1 Oct. 31, 2019

(30) Foreign Application Priority Data
Dec. 29, 2016 (KR) .................. 10-2016-0182977

(51) Int. Cl.
*A61B 17/3205* (2006.01)
*A61B 17/00* (2006.01)
(Continued)

(52) U.S. Cl.
CPC ............ *A61B 17/32053* (2013.01); *A61B 2017/00398* (2013.01); *A61B 2017/00761* (2013.01); *A61N 1/0502* (2013.01); *A61N 1/328* (2013.01)

(58) Field of Classification Search
CPC ........ A61B 17/32053; A61B 2090/062; A61B 2017/00761; A61B 2017/00398;
(Continued)

(56) References Cited

U.S. PATENT DOCUMENTS

| 2011/0009782 A1 | 1/2011 | Pampalone et al. |
| 2011/0092884 A1* | 4/2011 | Kang ............... A61B 18/14 604/21 |
| 2012/0158100 A1 | 6/2012 | Schomacker |

FOREIGN PATENT DOCUMENTS

| KR | 10-2009-0059988 A | 6/2009 |
| KR | 10-2010-0101420 A | 9/2010 |
| KR | 10-2014-0006169 A | 1/2014 |

OTHER PUBLICATIONS

International Search Report for PCT/KR2016/015579 dated Sep. 12, 2017 from Korean Intellectual Property Office.

* cited by examiner

*Primary Examiner* — Tan-Uyen T Ho
*Assistant Examiner* — Bridget E. Rabaglia
(74) *Attorney, Agent, or Firm* — Paratus Law Group, PLLC

(57) ABSTRACT

Disclosed is a skin treatment device, including: a support main body; a rotating part mounted on one surface of the support main body to be rotatable about a rotating shaft; a plurality of elastic parts which have one ends fixed to the support main body and inserted into the rotating part and are disposed to correspond to a rotation direction of the rotating part, and a needle holder coupled to tip ends of the elastic parts. When the rotating part rotates, the plurality of elastic parts are bent in the rotation direction so that relative positions of tip ends of the elastic parts vary.

6 Claims, 7 Drawing Sheets

(51) Int. Cl.
*A61N 1/05* (2006.01)
*A61N 1/32* (2006.01)

(58) Field of Classification Search
CPC .......... A61B 2017/00747; A61B 2017/00769;
A61B 2017/3407; A61B 2017/3409;
A61M 37/0015; A61N 1/328; A61N
1/0502; A61N 1/36017; A61N 1/0452;
A61N 1/0464; Y10S 128/907; A61H
39/086; A01K 11/005
See application file for complete search history.

SURGICAL DEVICE FOR SKIN THERAPY AND NEEDLE MODULE FOR SKIN THERAPY

ACKNOWLEDGEMENT

This work was supported by an Institute of Information & Communications Technology Planning & Evaluation (IITP) grant funded by the Korean government (MSIT) (No. 2018-0-00957, Development of multiple frequency 3D fractional RF devices for wrinkle treatment and various skin diseases).

CROSS-REFERENCE TO PRIOR APPLICATIONS

This application is a National Stage Patent Application of PCT International Patent Application No. PCT/KR2016/015579 filed on Dec. 30, 2016 under 35 U.S.C. § 371, which claims priority to Korean Patent Application No. 10-2016-0182977 filed on Dec. 29, 2016, which are all hereby incorporated by reference in their entirety.

BACKGROUND

The present invention relates to a skin treatment device, and more specifically, to a skin treatment device and a skin treatment needle module which allow elastic parts to be bent by a rotating part to perform a treatment procedure on curved skin to be treated by a predetermined depth so that relative positions of tip ends of the elastic parts vary.

Lately, various types of skin treatment procedure methods are being widely practiced. Generally, when skin sags and wrinkles, treatment procedures using needles have been widely used for the purpose of cosmetic restoration of a sagging and wrinkled part of the skin to be tight. As a non-surgical method, treatment procedures using a needle do not require an incision and simply put a thread through a corresponding portion of skin to be lifted so as to remove wrinkles.

A main cosmetic area in which the skin treatment procedure method is used is a face. Because the face has many curves, wrinkles are easily formed on the face. Further, since the face is an area visible to other people first, the face is an area that needs care first.

However, as described above, the face has many curves such that a skin treatment procedure is not easily preformed thereon. When a plurality of needles are used rather than one needle, it is more difficult to perform the skin treatment procedure according to the curves of skin. Therefore, when using the plurality of needles, a device that can easily perform a treatment procedure along curves of face skin by the uniform depth is required.

SUMMARY

The present invention is directed to providing a skin treatment device and a skin treatment needle module which allow a plurality of needles to be inserted to a uniform depth even when curves of skin vary.

One aspect of the present invention provides a skin treatment device which includes a support main body, a rotating part mounted on one surface of the support main body to be rotatable about a rotating shaft, a plurality of elastic parts which have one ends fixed to the support main body and inserted into the rotating part and are disposed to correspond to a rotation direction of the rotating part, wherein, when the rotating part rotates, the plurality of elastic parts are bent in the rotation direction so that relative positions of tip ends of the elastic parts vary, and a needle holder coupled to tip ends of the elastic parts.

The skin treatment device may further include a position maintaining unit that maintains a rotation position when the rotating part is rotated about the support main body.

The position maintaining unit may include a fixing groove formed in one surface of the support main body to be concave and a fixing unit which is mounted on the rotating part and insertion-coupled to the fixing groove.

One ends of the elastic parts may be fixed to an elastic part holder that is movable in a longitudinal direction of the elastic part by a driving unit of the support main body.

The driving unit may include a motor which is mounted on one surface of the support main body and generates power, a screw which is connected with the motor and rotates, and a nut which is coupled to the elastic part holder, wherein the nut may be moved in a longitudinal direction of the screw by screw-rotation of the screw to be coupled to the elastic part holder.

Another aspect of the present invention provides a skin treatment needle module which includes a plurality of skin therapy needles and a connector, to which the plurality of skin therapy needles are coupled, and which is attached to or detected from the above-described needle holder of the skin treatment device.

A skin treatment device and a needle module for a skin therapy according to the present invention can perform a treatment procedure on curved skin by a uniform depth.

A skin treatment device and a needle module for a skin therapy according to the present invention can easily adjust an angle thereof and perform a treatment procedure.

A skin treatment device and a needle module for a skin therapy according to the present invention can perform a three-dimensional treatment procedure.

DETAILED DESCRIPTION

Figure 1:
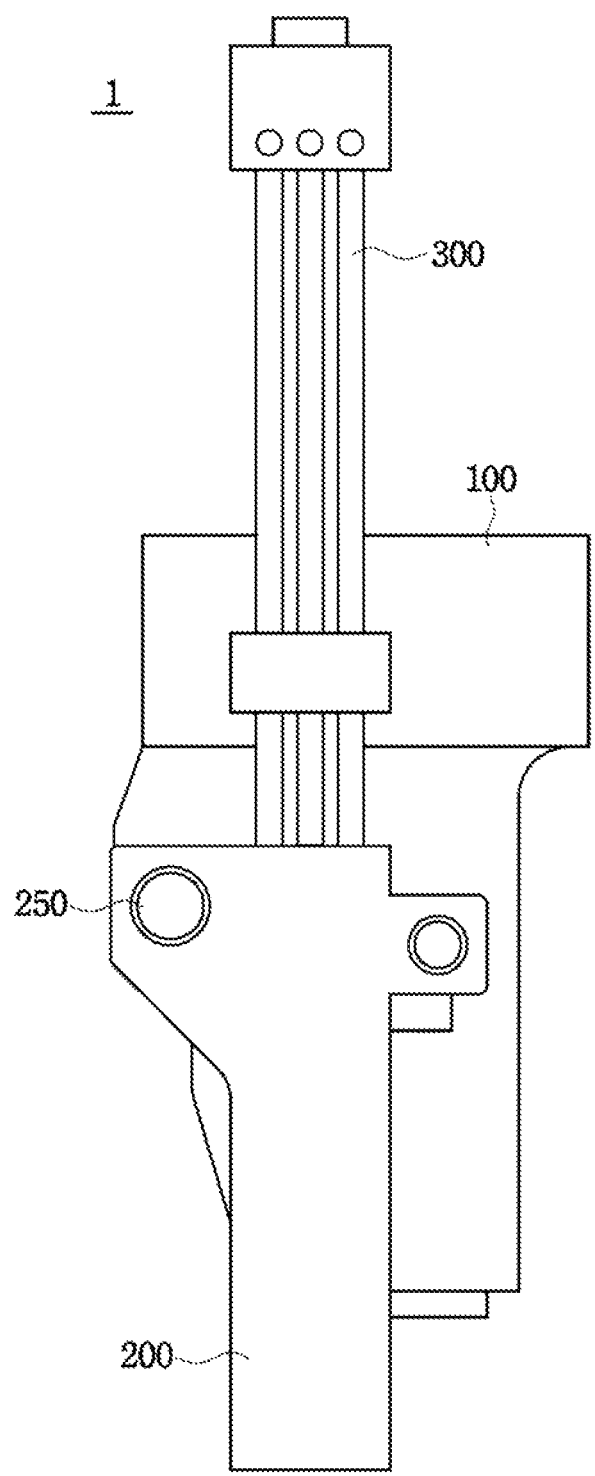
FIG. 1 is a view of a skin treatment device according to one embodiment of the present invention.

A skin treatment device according to embodiments of the present invention will be described with reference to the accompanying drawings in detail. While the invention is susceptible to various modifications and alternative forms, specific embodiments thereof will be shown by way of example in the drawings and described in detail therein. It should be understood, however, that there is no intent to limit the invention to the particular forms disclosed, but on the contrary, the invention is to cover all modifications, equivalents, and alternatives falling within the spirit and scope of the invention. In the description of each drawing, like reference numerals have been used for like elements. In the accompanying drawings, the dimensions of the structures are enlarged for clarity of the present invention and reduced for understanding the schematic configuration.

Further, although the terms first, second, and the like are used to distinguish one component from another component, the components are not limited by the terms. The terms are only used to differentiate one component from other components. For example, a first component may be referred to as a second component without departing from the scope of the present disclosure, and a second component may also be similarly referred to as a first component. Unless otherwise defined, all terms (including technical and scientific terms) used herein have the same meaning as commonly understood by one of ordinary skill in the art to which this invention belongs. It should be further understood that terms, such as those defined in commonly used dictionaries, should be interpreted as having a meaning that is consistent with their meaning in the context of the relevant art and are not to be interpreted in an idealized or overly formal sense unless expressly so defined herein.

Hereinafter, a skin treatment device and a needle module for a skin therapy will be described with reference to the accompanying drawings in detail.

Figure 2:
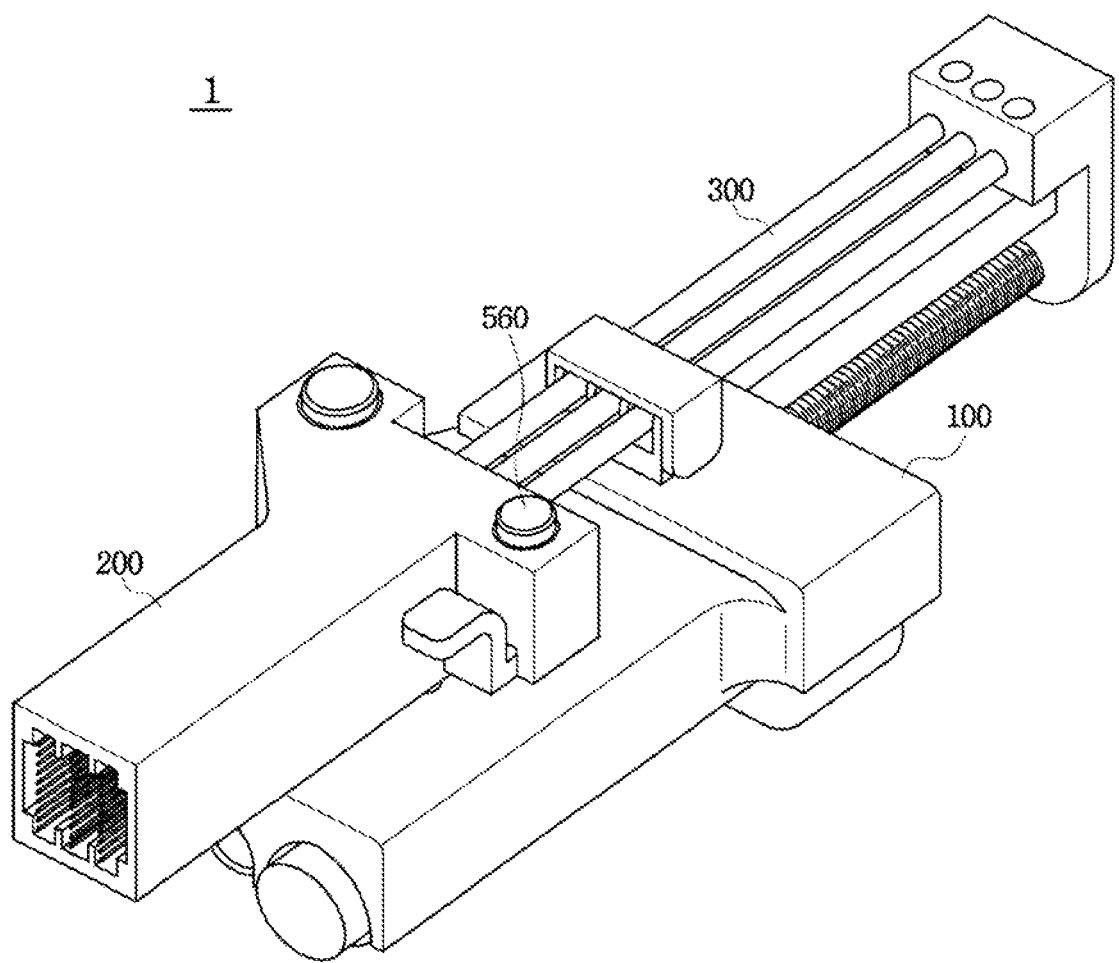
FIG. 2 is a perspective view of a skin treatment device according to one embodiment of the present invention.
Figure 3:
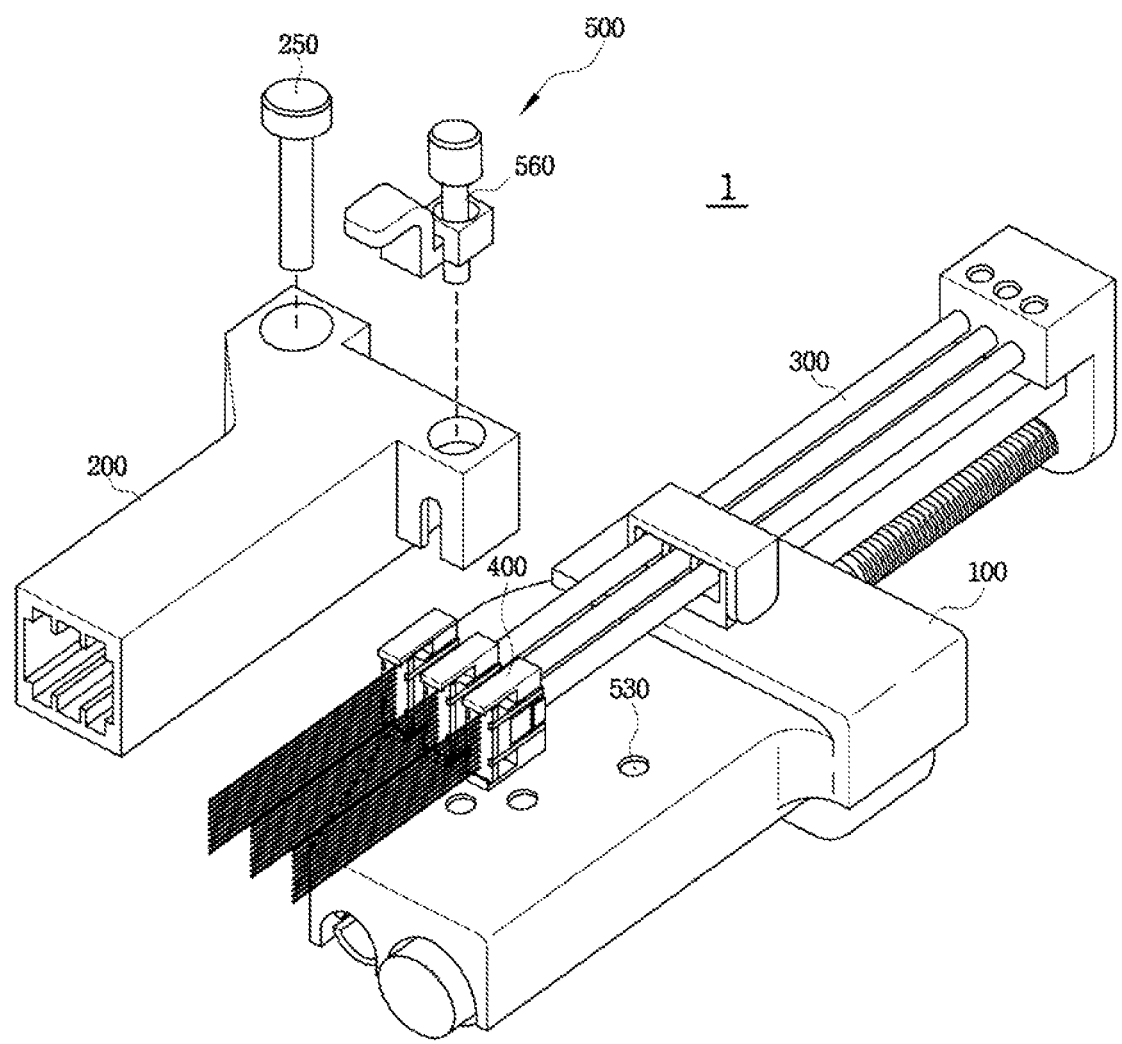
FIG. 3 is an exploded perspective view showing a rotating part according to one embodiment of the present invention in detail.
Figure 4:
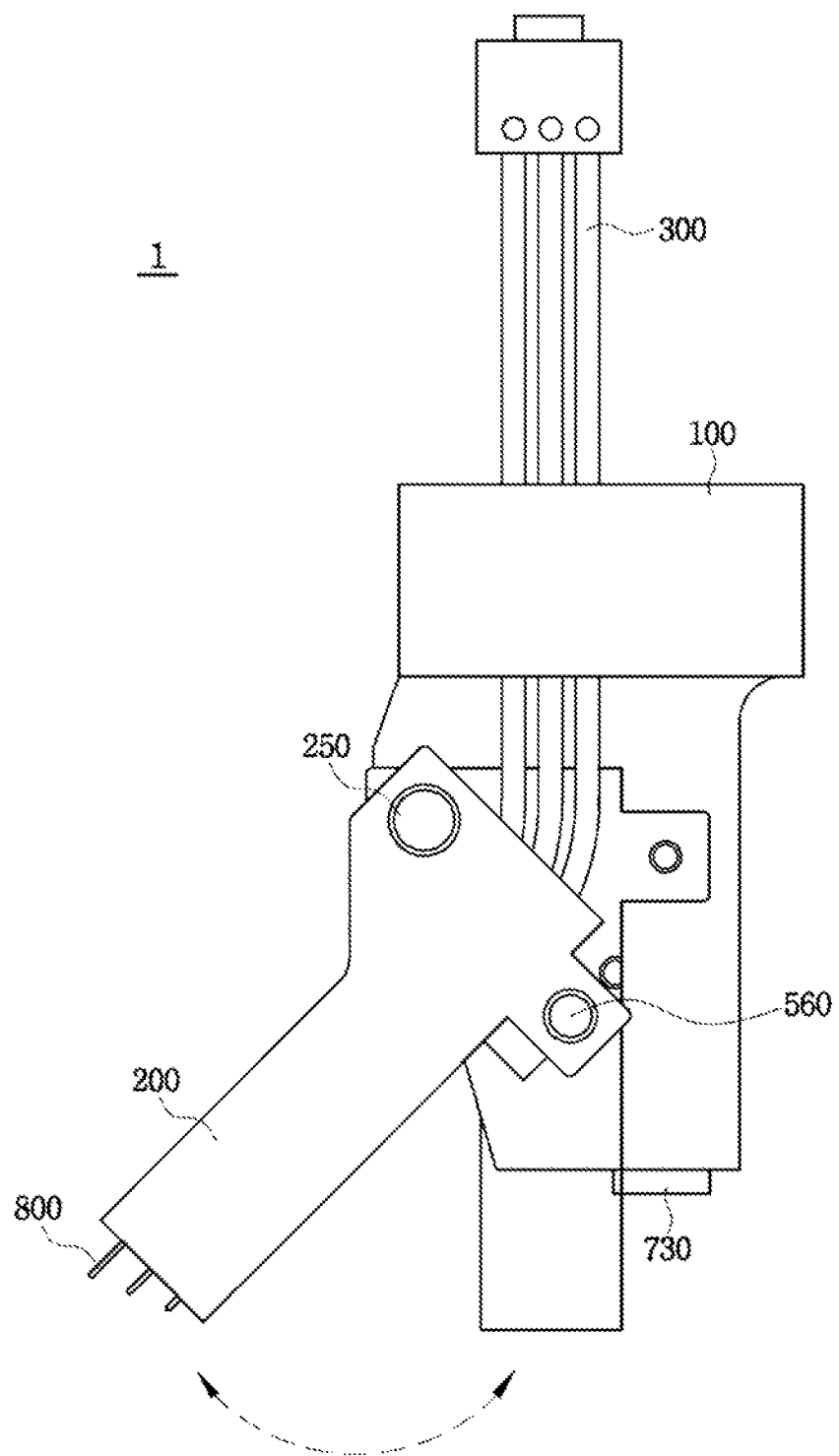
FIG. 4 is an operational view of the skin treatment device according to one embodiment of the present invention.

FIG. 1 is a view of a skin treatment device according to one embodiment of the present invention, FIG. 2 is a perspective view of a skin treatment device according to one embodiment of the present invention, FIG. 3 is an exploded perspective view showing a rotating part according to one embodiment of the present invention in detail, and FIG. 4 is an operational view of the skin treatment device according to one embodiment of the present invention.

A skin treatment device 1 according to one embodiment of the present invention includes a support main body 100, a rotating part 200 mounted on one surface of the support main body 100 to be rotatable about a rotating shaft 250, a plurality of elastic parts 300 which have one ends fixed to the support main body 100 and inserted into the rotating part 200 and are disposed to correspond to a rotation direction of the rotating part 200, and a needle holder 400 coupled to tip ends of the elastic parts 300, wherein, when the rotating part 200 rotates, the plurality of elastic parts 300 are bent in the rotation direction of the rotating part 200 so that relative positions of tip ends of the elastic parts 300 vary.

In the skin treatment device 1, the support main body 100 is a base device.

The rotating part 200 is mounted on one surface of the support main body 100 to be rotatable about the rotating shaft 250, and the rotating part 200 may be used as a manual type, which is operated by a user directly rotating the rotating part 200 with his or her hand or may be used as an automatic type by pressing a switch. Further, the rotating part 200 is mounted in the middle of the support main body 100 so as to rotate in two directions rather than in one direction.

The elastic parts 300 are insertion-mounted in the rotating part 200 and are bent when the rotating part 200 is rotated. The plurality of elastic parts 300 are disposed to correspond to the rotation direction of the rotating part 200, and relative positions of tip ends of the elastic parts 300 vary according to a rotation angle of the rotating part 200. When the rotating part 200 is rotated, the elastic part 300 that is closest to the rotating shaft 250 protrudes the farthest. Since the elastic part 300 is only bent without a change in length, the elastic part 300 protrudes in a stepped form like steps. The length of each of the elastic parts 300 may also be adjusted to a length desired by a user according to a distance when the plurality of elastic parts 300 are disposed to correspond to the rotation direction of the rotating part 200. Therefore, the elastic part 300 may be made of a bendable elastic material and may be bent into a shape like a spring. That is, since one ends of the elastic parts 300 are fixed to the support main body 100 but the tip ends thereof are not fixed, the elastic parts 300 protrude without extension.

The needle holder 400 is coupled to tip ends of the elastic parts 300, and in the skin treatment device, the needle holder 400 serves to fix the detachable needle module for a skin therapy. The needle holder 400 may be coupled to each of the elastic parts 300 so that relative positions of the tip ends of skin therapy needles 800, which are coupled with the needle holder 400, vary according to a degree in which each of the elastic parts 300 protrudes according to the rotation. In this case, since the plurality of skin therapy needles 800 are coupled to the needle holder 400 rather than one single skin therapy needle 800, the plurality of skin therapy needles 800 may have an appearance of a stepped form. Further, the needle holder 400 may connect all of the elastic parts 300 at once, and the elastic parts 300 allow relative positions of the tip ends of the skin therapy needle 800 to vary, and thus an angle of the needle holder 400 may be changed to be like a parallelogram. Therefore, the plurality of needles for skin therapy may protrude to be inclined according to the needle holder 400 rather than protrude to be stepped.

Meanwhile, the skin treatment device 1 further includes a position maintaining unit for maintaining a rotation position when the rotating part 200 is rotated about the support main body 100. In order for the position maintaining unit to maintain a position for an angle of rotation of the rotating part 200, the skin treatment device 1 according to one embodiment of the present invention includes a fixing unit 500 which includes a fixing groove 530 and a fixing pin 560, wherein the fixing groove 530 is formed in one surface of the support main body 100, and the fixing pin 560 is mounted in the rotating part 200 and insertion-coupled to the fixing groove 530. The fixing pin 560 may be coupled to the fixing groove 530 by an elastic body such as a spring, a damper, and the like. In this case, the fixing pin 560 may be fastened to or unfastened from the fixing groove 530. The fixing pin 560 may be coupled to the fixing groove 530 to pass through the support main body 100. When the fixing pin 560 coupled to the fixing groove 530 is pressed again or lifted, the coupling is released. After the release, the fixing pin 560 is moved to a desired position to be fastened again. The fixing groove 530 may be formed in the support main body 100 with a plurality of fixing grooves according to an angle, or a photo-interrupter or a sensor that detects a magnetic field may be attached to the fixing groove 530 to check the angle at which the fixing pin 560 is fastened. The signal of the fastening position detected by the sensor allows the current fastening position to be shown on a display device. When the photo-interrupter is used, a tip end of the fixing pin 560 that is inserted into the fixing groove 530 is painted with black that blocks light, and thus a light blocking effect can be increased. When a magnetic field detection method is used, a magnet is attached to a tip end of the fixing pin 560 to generate a signal that informs of the fastening position. The fixing unit 500, which includes the fixing pin 560 and the fixing groove 530, or the position maintaining unit may be formed according to the rotation direction of the rotating part 200, for example, to correspond to two directions of the rotating part 200, which is mounted to be rotatable in two directions, and may maintain a position of the rotating part 200 in various forms other than a pin form.

Figure 5:
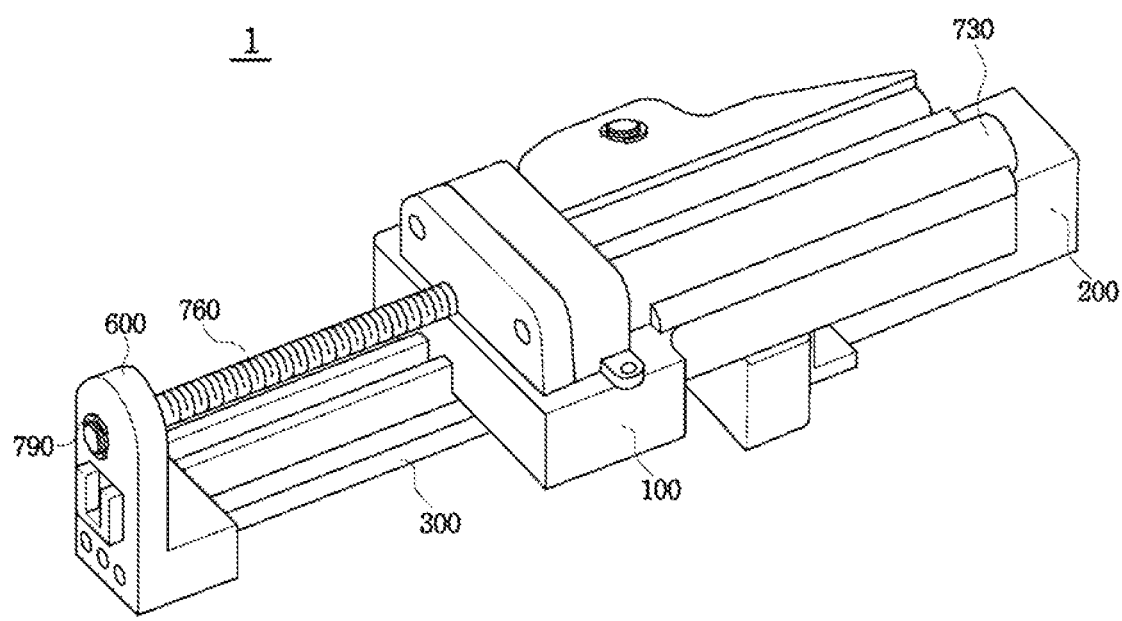
FIG. 5 is a rear view of the skin treatment device according to one embodiment of the present invention.
Figure 6:
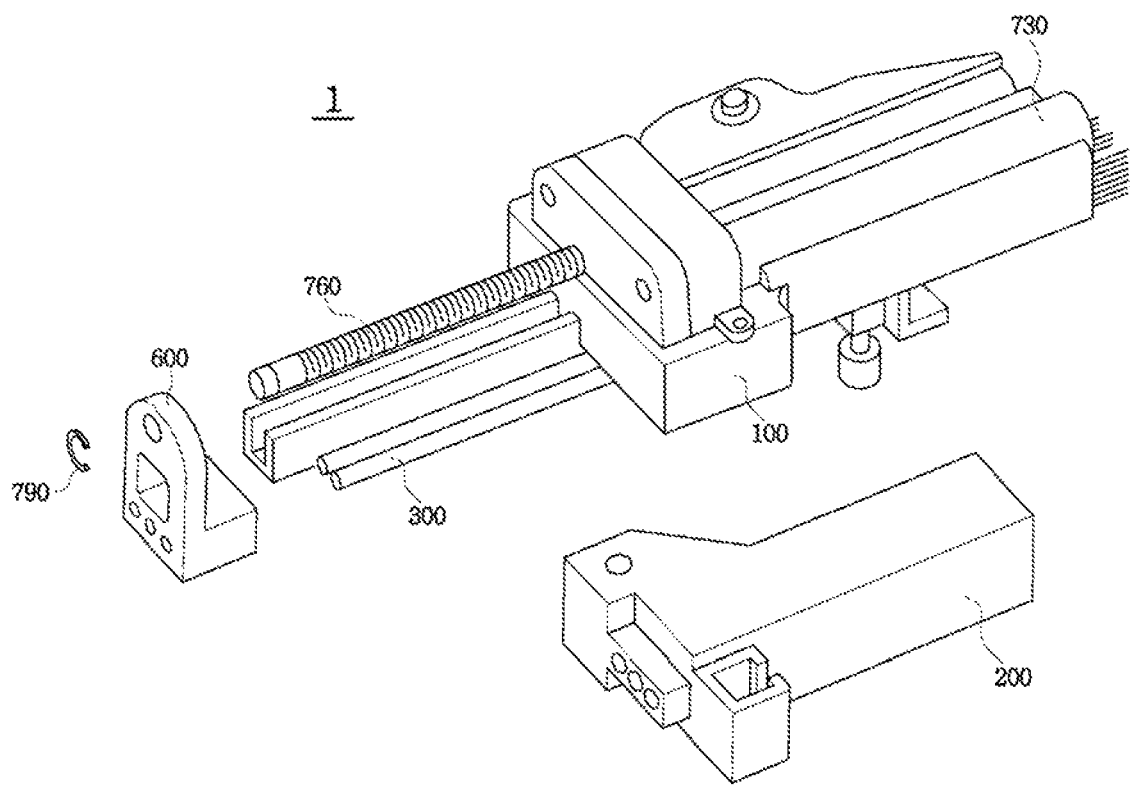
FIG. 6 is an exploded perspective view showing a driving unit according to one embodiment of the present invention in detail.

FIG. 5 is a rear view of the skin treatment device according to one embodiment of the present invention, and FIG. 6 is an exploded perspective view showing a driving unit according to one embodiment of the present invention in detail.

In the skin treatment device 1 according to one embodiment of the present invention, one ends of the plurality of elastic parts 300 are fixed to an elastic part holder 600 that is movable in a longitudinal direction of the elastic part 300 by a driving unit of the support main body 100. One ends of the elastic parts 300 are fixed to the elastic part holder 600 that is movable, and the movement direction of the elastic part holder 600 is a longitudinal direction of the elastic part 300. In a skin treatment procedure, the needles for a skin therapy are manually pressed by skin but are also automatically moved forward or backward by the driving unit. The driving unit automatically moves forward or backward to perform the skin treatment procedure to a uniform depth. Therefore, the skin treatment procedure can be more accurately performed.

Further, the skin treatment device 1 according to one embodiment of the present invention includes a motor 730 which is mounted on one surface of the support main body 100 and generates power, a screw 760 which is connected with the motor 730 and rotates, and a nut 790 which is coupled to the elastic part holder 600, moved in a longitudinal direction of the screw 760 by screw-rotation of the screw 760, and coupled to the elastic part holder 600.

The motor 730 is mounted on one surface of the support main body 100, generates power, and transfers the power to the screw 760. In this case, the motor 730 may directly transfer the power, or gears for reducing a speed thereof may be included in the skin treatment device 1.

The screw 760 receives the power generated by the motor 730 and rotates.

The nut 790 that is coupled to the elastic part holder 600 may be coupled to a groove formed in the elastic part holder 600 and may be coupled to an upper portion of the elastic part holder 600. The nut 790 is coupled to the movable elastic part holder 600 to be moved by rotation of the screw 760. As the nut 790 is moved, the elastic part 300 coupled to the elastic part holder 600 is moved in a longitudinal direction.

Figure 7:
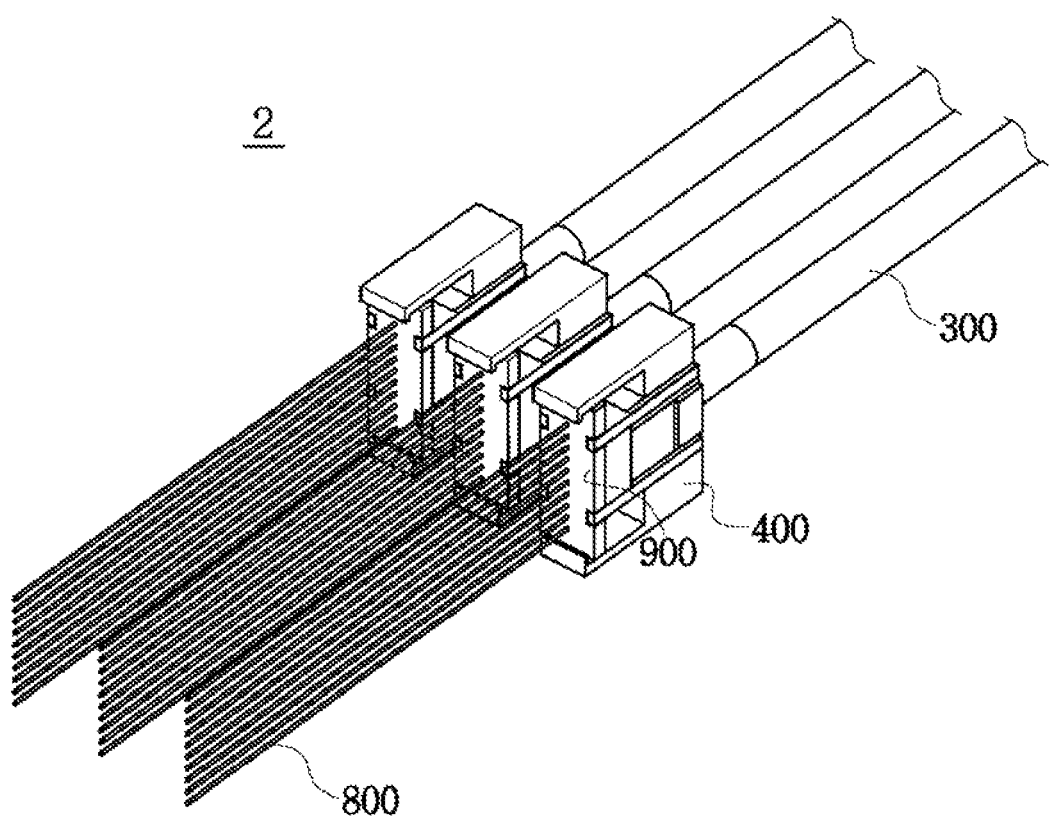
FIG. 7 is a view of a needle module for a skin therapy according to one embodiment of the present invention.

FIG. 7 is a view of a needle module for a skin therapy according to one embodiment of the present invention.

A needle module for a skin therapy 2 includes a plurality of skin therapy needles 800 and a connector 900 to which the plurality of skin therapy needles 800 are coupled and which are attached to or detached from the needle holder 400 of the above-described skin treatment device 1.

The needle module for a skin therapy 2 includes the skin therapy needle 800 and the connector 900 to which the plurality of skin therapy needles 800 are coupled, wherein the connector 900 may be attached to or detached from the needle holder 400 of the skin treatment device 1. When the skin therapy needles 800 use high frequency, the connector 900 may be formed of a substrate. Further, to generate electric energy, a unit for generating electric energy may be further included in the skin treatment device 1, and thus the needle holder 400 and the plurality of elastic parts 300 may include the unit for generating electric energy. The elastic part 300 may include an electric wire that transfers electric energy, and a spring may be coupled to the outside of the wire to maintain a shape of the elastic part 300. In the needle module for a skin therapy 2, the connector 900 is attached to or detached from the needle holder 400 and is manufactured as a consumable for cleanliness of skin treatment.

Although the exemplary embodiments of the present invention have been described above, various changes, modifications and equivalents may be used. It is clear that the present invention may be properly modified and equally applied to the above embodiments. Therefore, the above description does not limit the scope of the present invention which is defined by the limitations of the following claims.

The skin treatment device and a skin treatment needle module can perform a skin treatment procedure even on curved skin to a uniform depth and easily adjust an angle thereof to perform a skin treatment procedure.

The invention claimed is:

1. A skin treatment device comprising:
a support main body;
a rotating part mounted on one surface of the support main body to be rotatable about a rotating shaft;
a plurality of elastic parts each of which have one end fixed to the support main body and inserted into the rotating part and are disposed to correspond to a rotation direction of the rotating part, wherein, when the rotating part rotates, the plurality of elastic parts are bent in the rotation direction so that relative positions of tip ends of the elastic parts vary;
and a needle holder coupled to tip ends of the elastic parts.

2. The skin treatment device of claim 1, further comprising a position maintaining unit that maintains a rotation position when the rotating part is rotated about the support main body.

3. The skin treatment device of claim 2, wherein the position maintaining unit includes a fixing groove formed in one surface of the support main body to be concave and a fixing unit which is mounted on the rotating part and insertion-coupled to the fixing groove.

4. The skin treatment device of claim 1, wherein one end of each of the elastic parts are fixed to an elastic part holder that is movable in a longitudinal direction of the elastic part by a driving unit of the support main body.

5. The skin treatment device of claim 4, wherein the driving unit includes a motor which is mounted on one surface of the support main body and generates power, a screw which is connected with the motor and rotates, and a nut which is coupled to the elastic part holder, wherein the nut is moved in a longitudinal direction of the screw by screw-rotation of the screw to be coupled to the elastic part holder.

6. A skin treatment needle module comprising:
a plurality of skin therapy needles; and
a connector to which the plurality of skin therapy needles are coupled and which is attached to or detached from the needle holder of the skin treatment device according to claim 1.

* * * * *